United States Patent [19]

Cooper et al.

[11] Patent Number: 5,506,679
[45] Date of Patent: Apr. 9, 1996

[54] NEPHELOMETER INSTRUMENT

[75] Inventors: Richard J. Cooper, Loveland; Kevin A. Keilbach, Ft. Collins; Richard P. Kolman; Ernie R. Paoli, both of Loveland; Kenneth L. Stutzman; Robert D. Stream, both of Ft. Collins, all of Colo.

[73] Assignee: Hach Company, Loveland, Colo.

[21] Appl. No.: 303,176

[22] Filed: Sep. 8, 1994

[51] Int. Cl.⁶ ................................................. G01N 21/00
[52] U.S. Cl. .......................... 356/338; 356/339; 356/343; 356/342
[58] Field of Search ................................. 356/335–343, 356/244, 246, 432, 436, 440, 442; 250/573, 576, 574, 575

[56] References Cited

U.S. PATENT DOCUMENTS

| | | | |
|---|---|---|---|
| 3,078,756 | 2/1963 | Barton et al. | 356/339 |
| 3,785,735 | 1/1974 | Friedman et al. | 356/339 |
| 4,250,394 | 2/1981 | O'Connor | 356/340 |
| 5,231,378 | 7/1993 | Dennis et al. | 356/338 |

Primary Examiner—Hoa Q. Pham
Attorney, Agent, or Firm—Dean P. Edmundson

[57] ABSTRACT

A nephelometer instrument capable of measuring from zero to 10,000 NTUs. The instrument includes four light detectors, three of which are positioned such that they measure light scattered at specific directions by a liquid sample. The fourth detector measures light transmitted through the sample. A removable light filter is also included. The light beam is focused on the front surface of the sample cell.

1 Claim, 15 Drawing Sheets

NEPHELOMETER INSTRUMENT

FIELD OF INVENTION

This invention relates to nephelometer instruments useful for measuring turbidity in liquids. More particularly, this invention relates to instruments capable of accurately measuring turbidity of a highly-turbid fluid.

BACKGROUND OF THE INVENTION

Although nephelometer instruments for measuring turbidity of liquids have been commercially available for many years, such instruments have been somewhat limited in their ability to measure turbidity of highly-turbid liquids. As the turbidity of a liquid increases, light has a more difficult time passing through the liquid. When the turbidity is too high, enough light cannot pass through to enable an accurate measurement of turbidity to be made. Errors in measurement therefore increase. Consequently, in order to measure highly-turbid liquids, it has been necessary to first dilute the highly-turbid liquid and then measure the turbidity of the diluted sample. The highest level of turbidity measurement which is possible with existing laboratory instruments is about 2000 NTU. Although a highly-turbid liquid sample may be diluted and then measured using existing instruments, this requires that the technician be very careful and accurate in making the dilution. Also, diluting the sample requires extra time and equipment and can physically change the sample. Thus, diluting the sample is not a preferred procedure.

Another limitation of commercially-available nephelometers is that they are not capable of measuring color in a liquid. The measurement of color in water is especially important, for example, in potable water. Further, measurement of color in a liquid is important in various industrial processes.

There has not heretofore been provided an improved nephelometer instrument having the advantages and features described herein.

SUMMARY OF THE INVENTION

In accordance with the present invention there is provided an improved nephelometer instrument which is capable of measuring from zero to 10,000 Nephelometric Turbidity Units (NTUs) in addition to being capable of directly displaying Nephelos and European Brewing Conventions (EBCs). The instrument also provides the user with the choice of using either a ratio or non-ratio method of measurement.

Additionally, the user can program into the instrument one or two of his own units of measurement based on NTU turbidity. Thus, the user can use his own standards for measuring turbidity of a liquid. This enables a user to report data in his own selected units.

A further object of the invention is to provide a nephelometer capable of providing direct measurement of color in a liquid sample utilizing color filters mounted in an interchangeable plastic holder. Colored samples can be read in absorbance (A), transmittance (% T), or cobalt platinum color unit (CU) reading modes.

Another object of the invention is to provide a nephelometer utilizing a novel natural convection method of cooling to remove internal heat generated by a halogen light source and instrument power supply.

Yet another object of the invention is to provide a nephelometer using a halogen light source which is mounted in a novel manner to allow easy replacement while providing accurate placement of the light source filament.

It is a further object of this invention to provide a nephelometer which includes an integral paper printer which is mounted in the instrument housing using a novel retention technique.

The advantages and features of the nephelometer of this invention will be apparent from the following detailed description and the accompanying drawings.

BRIEF DESCRIPTION OF THE DRAWINGS

The invention is described in more detail hereinafter with reference to the accompanying drawings, wherein like reference characters refer to the same parts throughout the several views and in which.

DETAILED DESCRIPTION OF THE INVENTION

Figure 1:
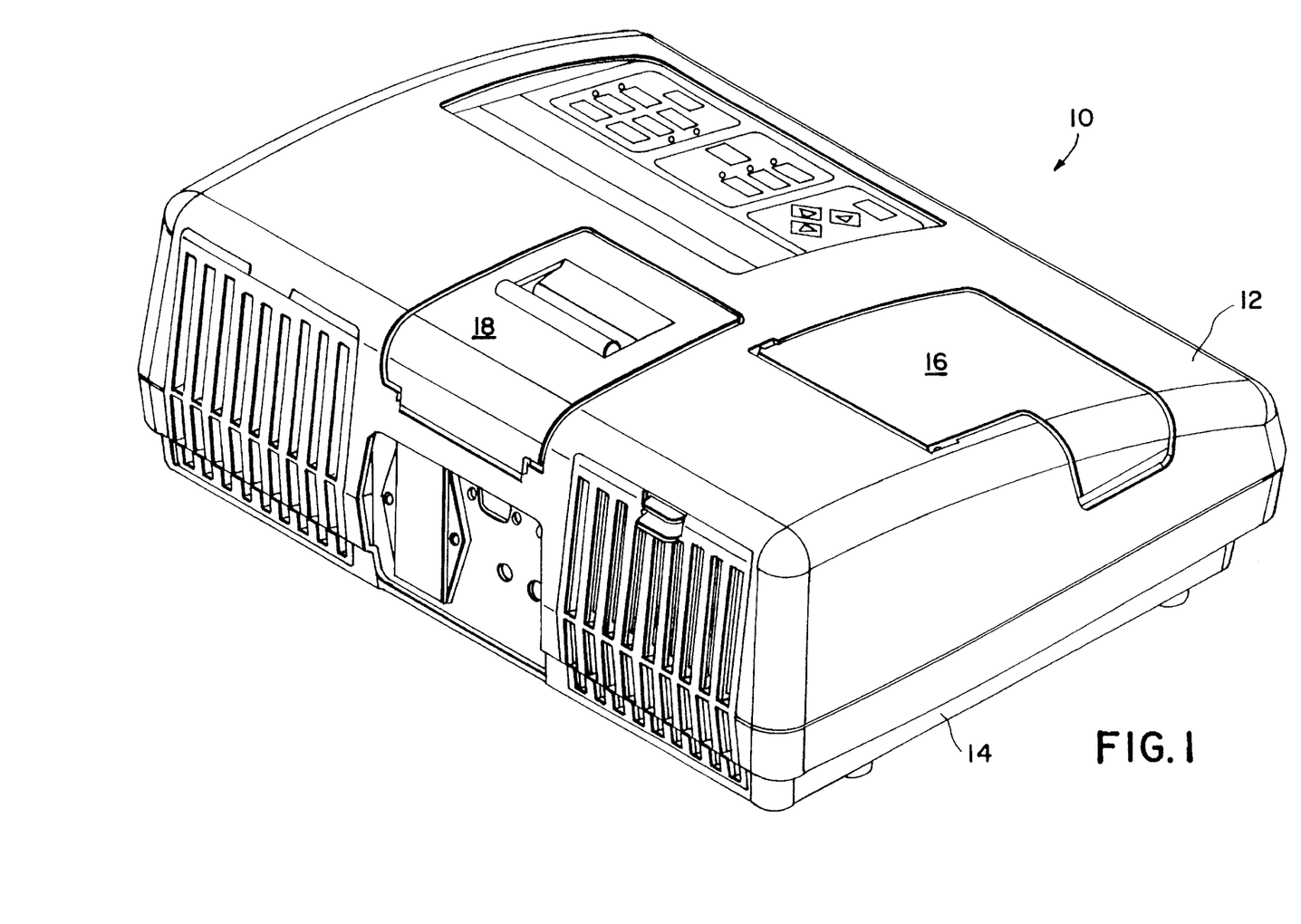
FIG. 1 is a perspective view of one embodiment of nephelometer instrument of the invention.
Figure 1A:
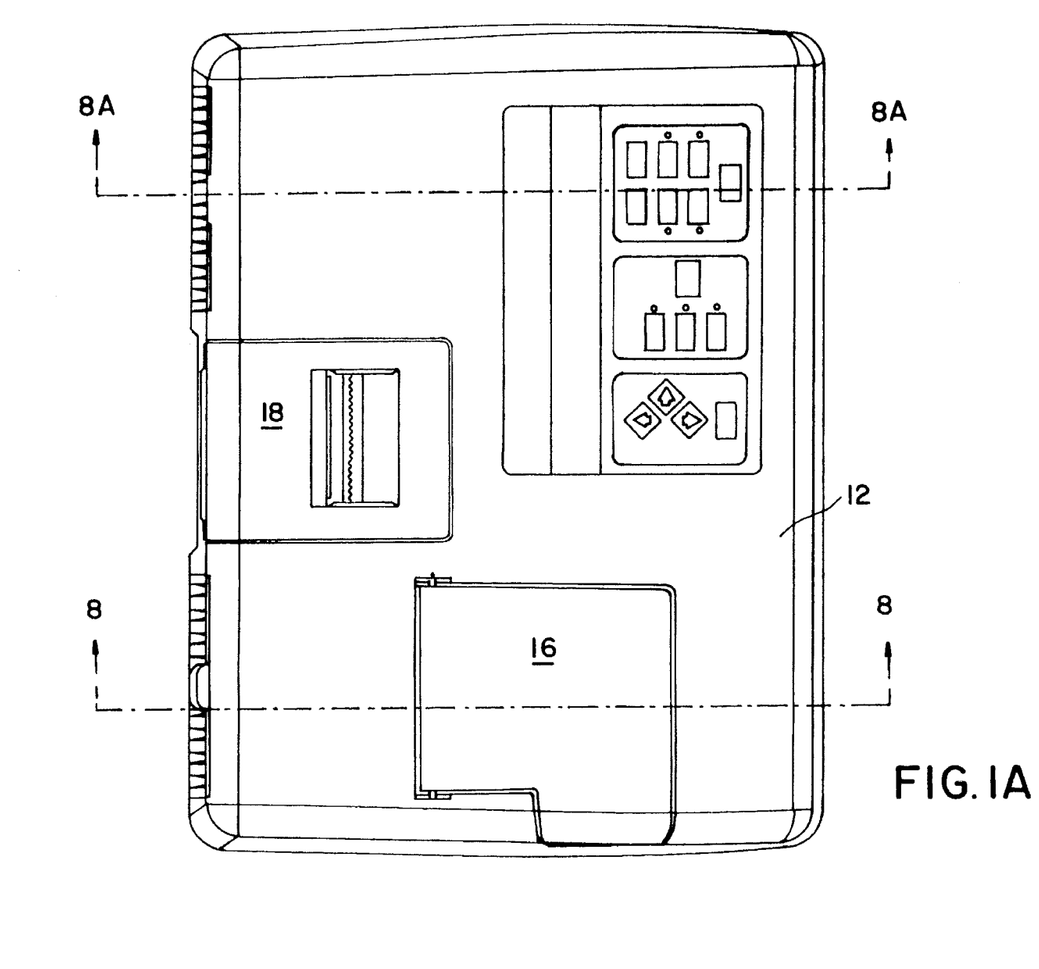
FIG. 1A is a top view of the instrument of FIG. 1.
Figure 2:
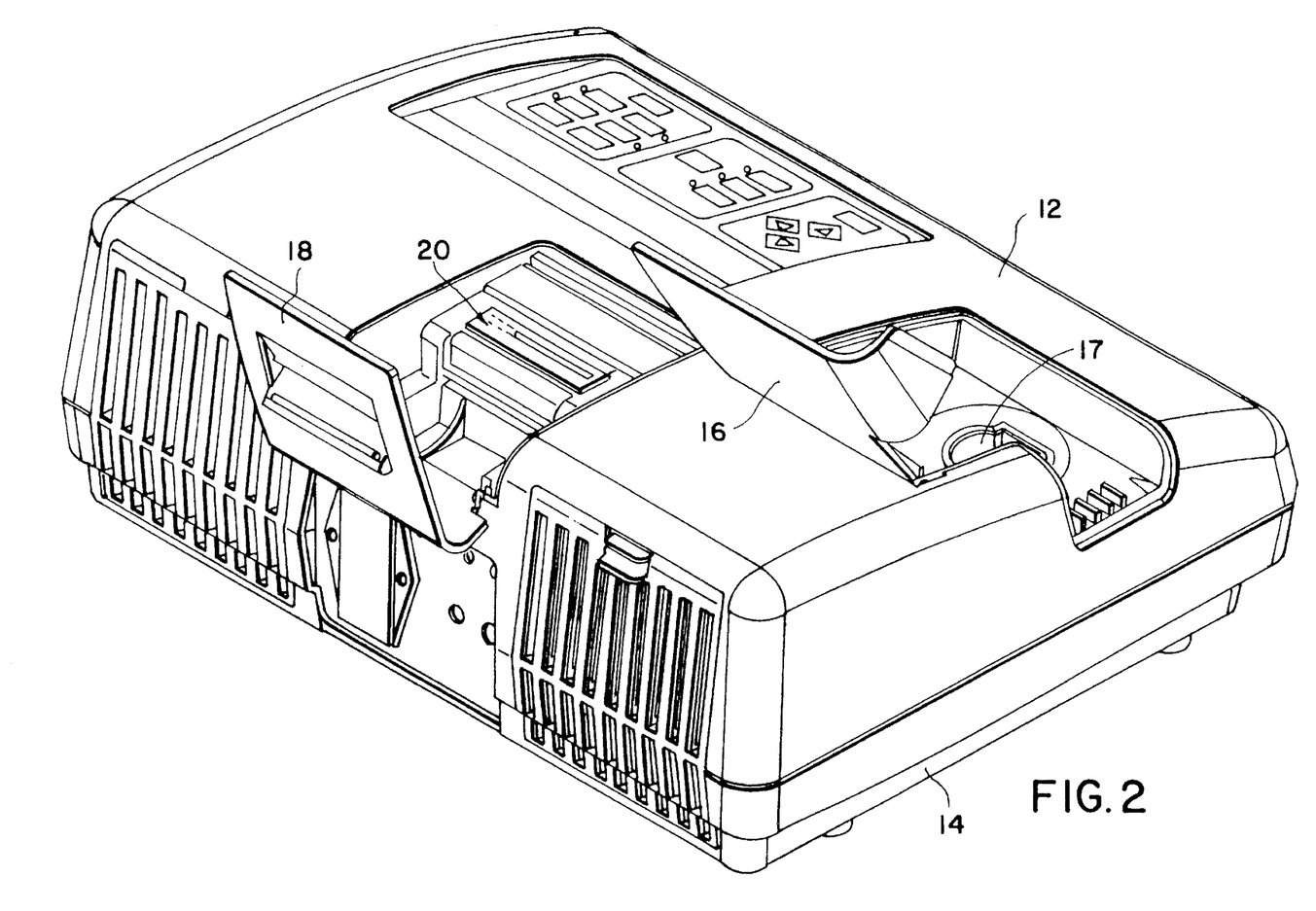
FIG. 2 is a perspective view of the instrument of FIG. 1 with a cover open to reveal the opening in which a sample cell is received for testing and another cover open to reveal the integral printer.
Figure 3:
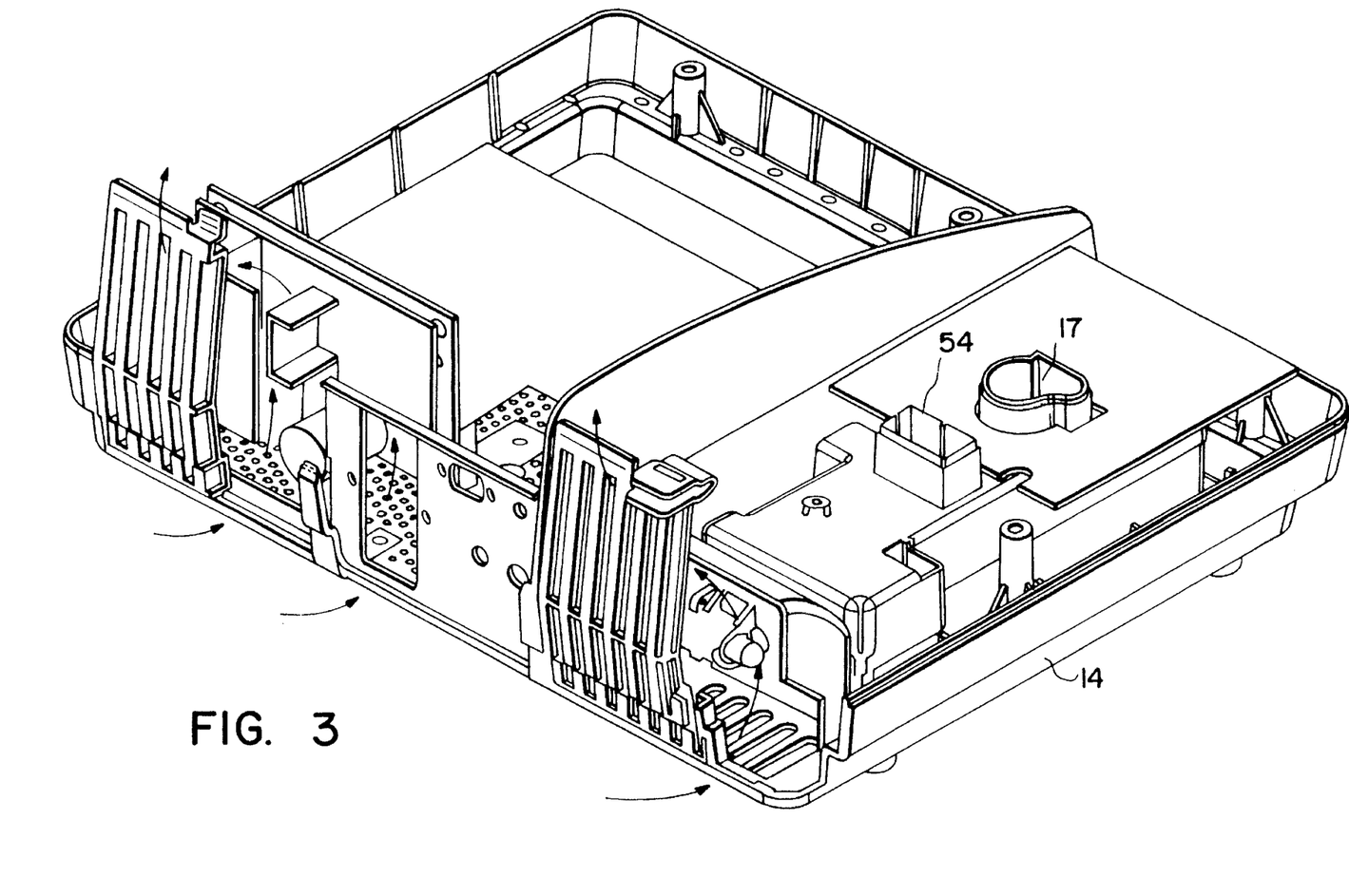
FIG. 3 shows the instrument of FIG. 1 with the upper portion of the housing removed to reveal the interior of the instrument.

In the drawings there is shown one embodiment of improved nephelometer instrument 10 of the invention. The instrument includes an upper housing member 12 and a lower housing member 14. The upper housing includes a hinged door or cover 16 (shown in open position in FIG. 2). Cover 16 covers the receiving opening 17 for receiving a sample cell for testing the turbidity of a liquid.

Hinged door 18 (shown in open position in FIG. 2) provides access to an integral printer 20 in the upper housing member.

Figure 4:
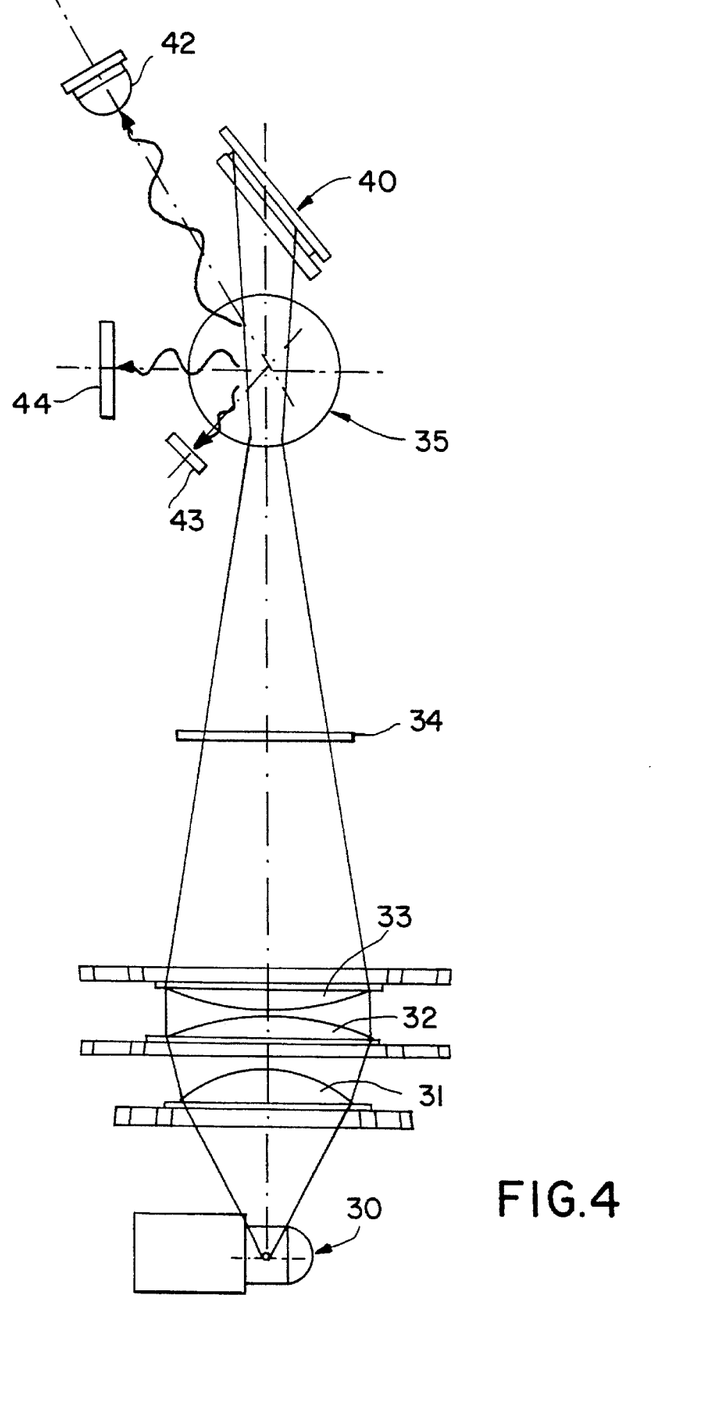
FIG. 4 is a top view showing the optical system used in the instrument of FIG. 1 and the light path from the source through the sample cell and to the detectors.
Figure 5:
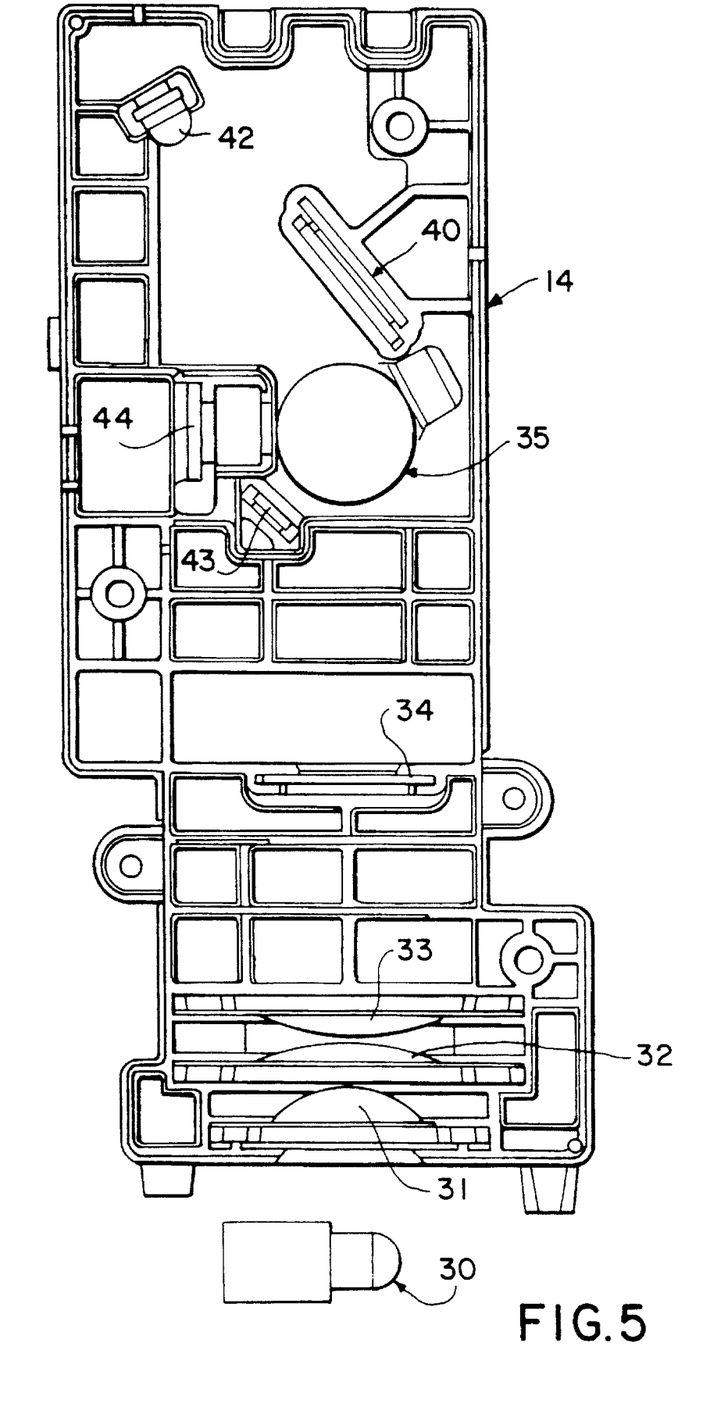
FIG. 5 is a top view of the instrument optics, with the upper portion of the optics housing removed, showing the placement and arrangement of the optical components.
Figure 6:
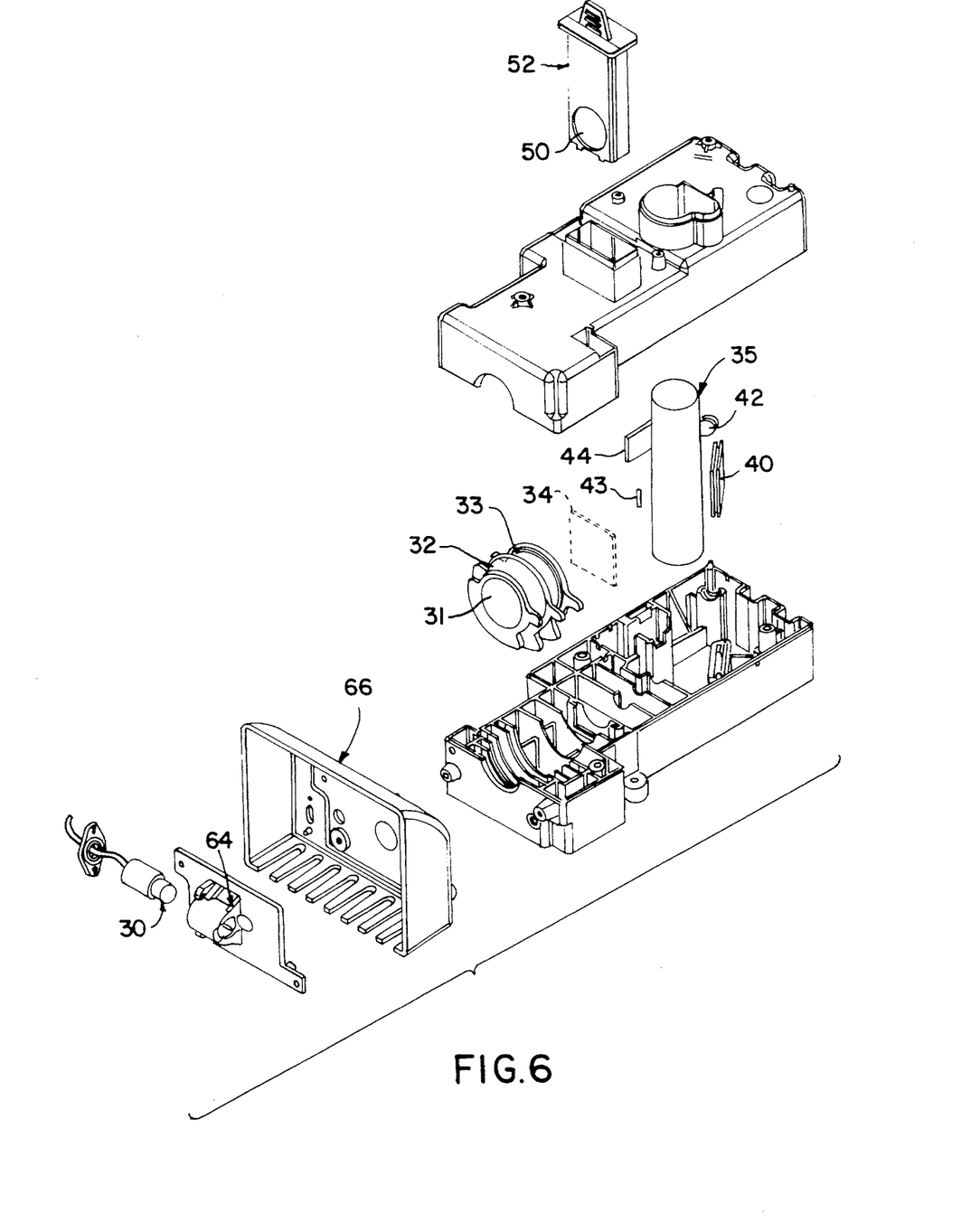
FIG. 6 is an explosion view showing the optical components of the instrument of FIG. 1.

The optical light path from the lamp or light source 30 through the lenses 31, 32 and 33, and light filter 34, and sample cell 35 is shown in FIG. 4. Transmitted light is measured by detector 40. Scattered light is detected by each of detectors 42, 43 and 44. Detector 42 measures forward-scattered light, detector 43 measures back-scattered light, and detector 44 measures 90° scattered light. Non-ratio turbidity measurements utilize only the 90° detector. Ratio turbidity measurements utilize all four of the detectors. Only the transmitted light detector 40 is utilized for transmittance, absorbance and color unit measurements.

The measurement of turbid fluid up to about 10,000 NTU's is possible because of the optical design utilizing three lenses and the four light detectors. Light from the tungsten halogen lamp 30 is collected by the three lenses 31, 32 and 33 which focus the light and reduce stray light. Lens 31 has one convex and one concave side which align the light rays onto lens 32. Lenses 32 and 33 are the same with two convex surfaces mounted in face-to-face relation so that they act in tandem to precisely focus the light on the front surface of the sample cell 35.

A series of baffles in the path between the lenses and the sample cell catch light scattered from the lens surface to help prevent any stray light from impinging upon the detectors. All but the baffle closest to the sample cell are sized so that the caustic that surrounds the light from the lenses just touches the baffle edges. The final baffle (closest to the sample cell) is oversized so that any misalignment of the beam will not cause the edges of the baffle to glow and increase the instrument stray light.

In normal turbidity reading modes, a removable blue "IR" glass filter 34 is placed in the light path between the lenses and the sample cell. This causes the detector response to peak at a wavelength of between 400 nm and 600 nm in compliance with U.S. EPA guidelines (EPA Method 180.1).

In the sample cell area of the optics there are four detectors and one light filter. It is the arrangement of these detectors which allow the instrument to measure up to 10,000 NTU's. A large "transmitted" detector 40 located on the axial light beam path measures the light that passes through the sample. A "neutral density" glass filter directly in front of the detector attenuates the light above 600 nm which is incident on this detector and the combination is canted at 45 degrees to the incident light path so that reflections from the surface of the filter and detector do not re-enter the sample cell area. A "forward scatter" detector 42 measures the light scattered at 30 degrees nominal from the transmitted direction. A detector 44 at 90 degrees nominal to the incident light path and out of the plane formed by the light beam and the other detectors measures light scattered from the sample normal to the incident beam. The angle and baffling for this 90 degree detector blocks light scattered directly from the side of the sample cell while collecting light scattered from the light beam and refracted into the detector. A small "back-scatter" detector 43 mounted 138 degrees from the incident light path measure light scattered by very turbid samples when the other detectors no longer produce a signal linear with turbidity. This fourth detector extends the measurement range of the turbidimeter to 10,000 NTU. The light energy impinging on each of the four detectors is electronically combined to calculate the turbidity of the sample.

This invention can operate in one of two pre-set methods. One method is the "ratio off" mode where measurements of turbid fluid are taken using only the 90 degree detector 44. This method may be required by certain government agencies and is most applicable for values less than 40 NTU. The second method is the "ratio on" mode where the 90 degree detector signal is ratioed against the signals from the other three detectors. This method allows for the measurement of very turbid fluids, up to 10,000 NTU's. Previous instruments have been capable of using one or the other of the methods described above, but not the choice of two in the same instrument.

In addition, the user can program into the instrument two user defined measurement units using up to three letters or numbers on the digital display screen. These two new units are linear conversion factors based on the NTU measurement units, with up to 8 points defining line segments.

Figure 7:
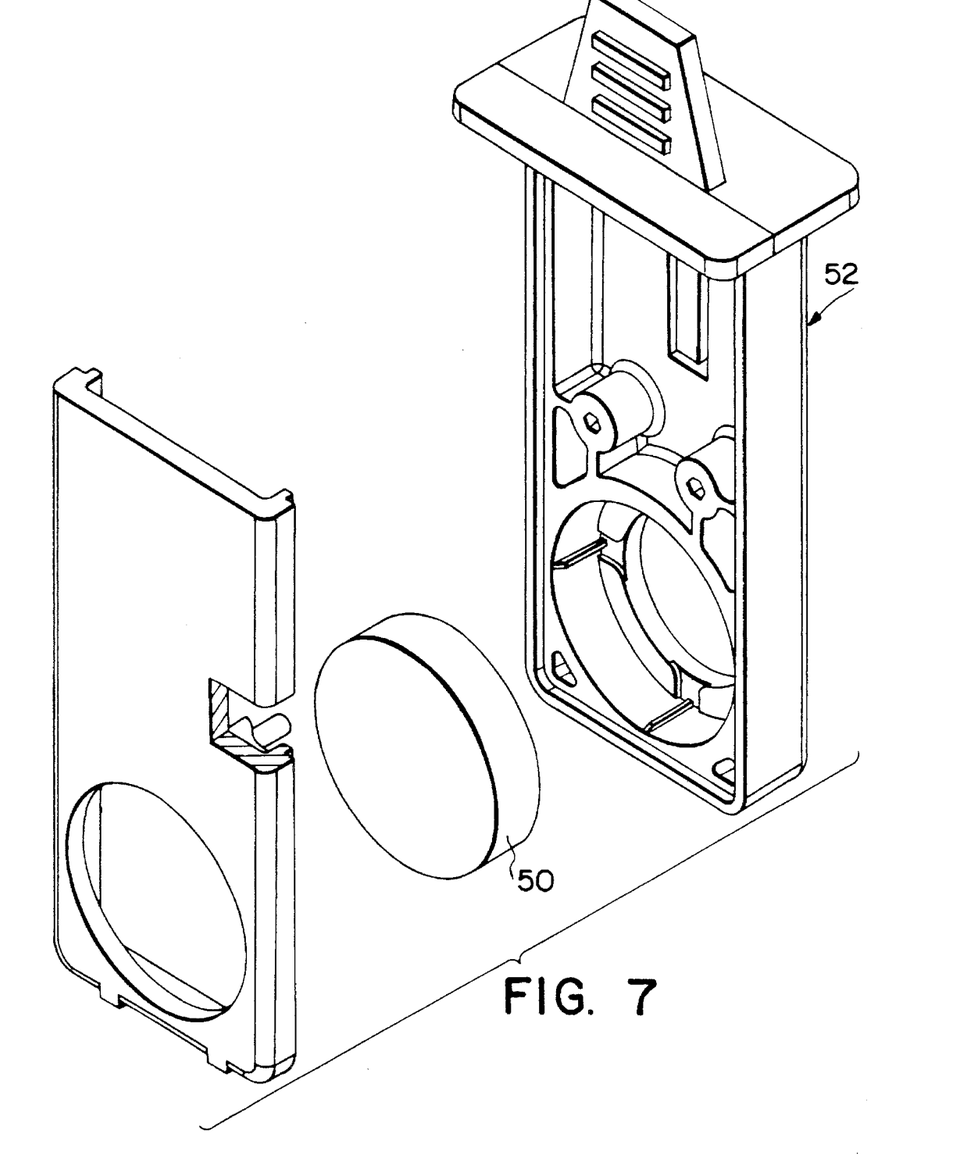
FIG. 7 shows one embodiment of a light filter module useful in the instrument of this invention.

A removable interference filter 50 may be used in the filter holder in place of the blue "IR" filter 34 so turbidity measurements can be made with "quasi" monochromatic light. This filter allows the instrument to provide direct measurement of color in Absorbance (A), Transmittance (% T) or Cobalt Platinum Color Unit (CU) reading modes. The circular glass filter 50 is pressed into one half of the filter holder 52 and is held to this holder by four crushable ribs. The other half of the holder is pressed into this filter half and held together by friction. This complete filter/holder is inserted into the optics assembly between the light source and the sample cell through a rectangular opening 54 in the outside enclosure which envelops a raised rectangular area in the optics assembly. This nesting of the various assemblies prevents outside ambient light from entering the optics assembly.

Figure 8:
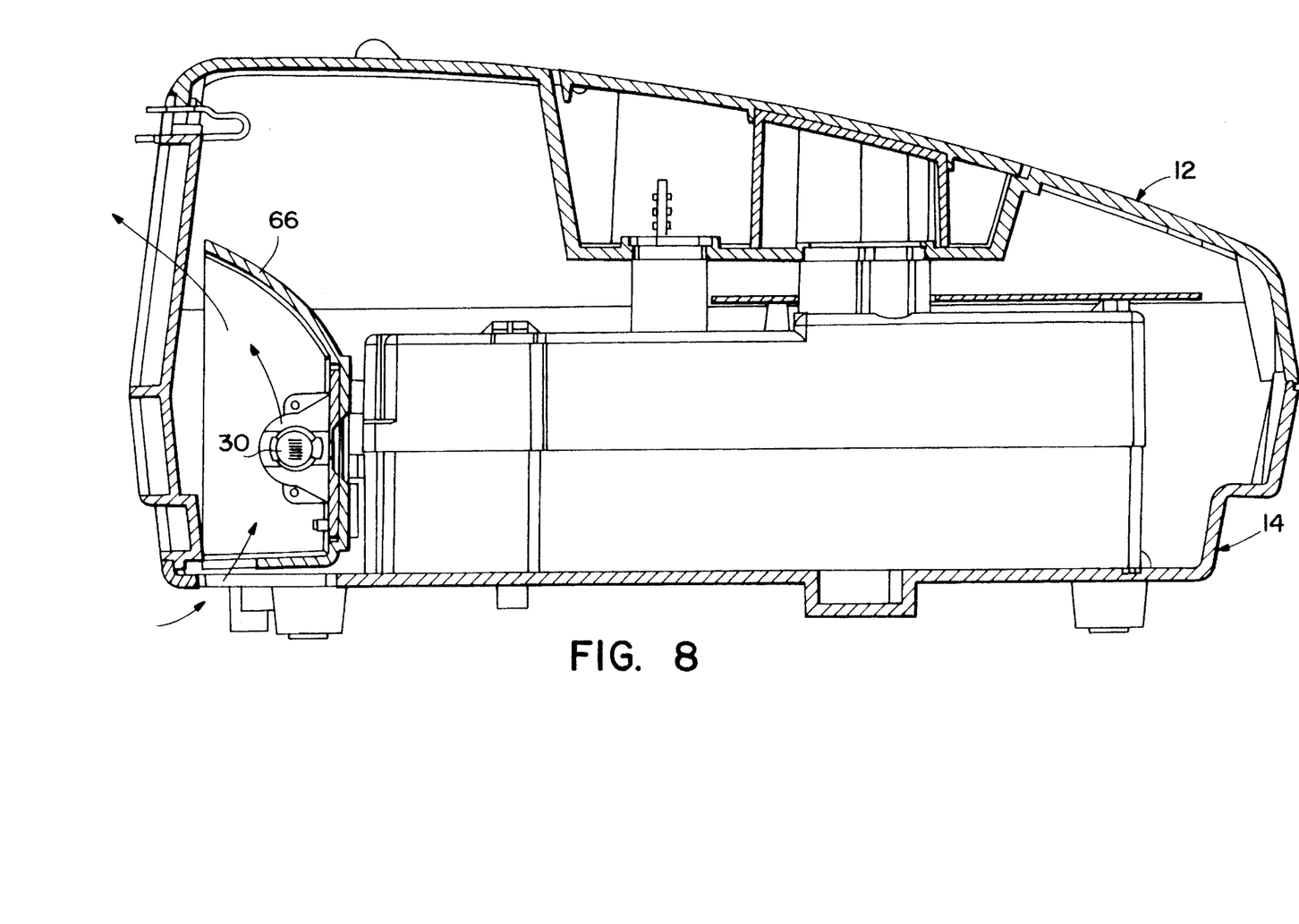
FIG. 8 is a cross-sectional view of the instrument taken along line 8—8 in FIG. 1A showing the manner in which air can pass through the rear of the housing to dissipate heat.

FIG. 8 is a cross-sectional view of the instrument showing the manner in which air is able to enter the housing through the base near the back of the instrument, pass over the halogen lamp 30, and then exit the housing through the upper portion of the back wall of the housing. Deflector or heat shield 66 directs the air rising over the lamp toward the upper portion of the back wall. This natural air convection cools the lamp. When the lamp 30 is energized, surrounding ambient air is heated and starts to rise. This heated air continues to rise vertically until encountering the surface of the heat shield 66. The upper portion of the heat shield is curved towards the rear of the instrument to direct heated air away from the precision optical assembly and electronic circuitry. When this heated air encounters the rear of the instrument, it is released to the outside through a stepped, slotted door which also prevents accidental fluid spillage from entering the lamp compartment. This heated air from the lamp is replaced by cool outside ambient air directly below the lamp through a series of slots in the instrument base. This cool air is directed around another set of slots in the base of the heat shield. This overlapping of the two sets of slots will prevent any hot, hazardous material from escaping outside the instrument should the lamp fail or burst. Additional cool, ambient outside air is drawn into the instrument through the bottom portion of the lamp door and through a series of holes around the housing base. The top and vertical sides of the lamp shield are in close proximity to the vertical rear housing walls of the instrument to prevent any heated air from escaping into the main body of the instrument. Due to the high air temperatures generated by the halogen lamp, the lamp holder and heat shield are constructed from high heat resistant composite material to prevent deformation and degradation. The lamp body is further cooled by two large slots in the lamp holder which direct cool ambient air around the cylinder holding the lamp body.

Figure 8A:
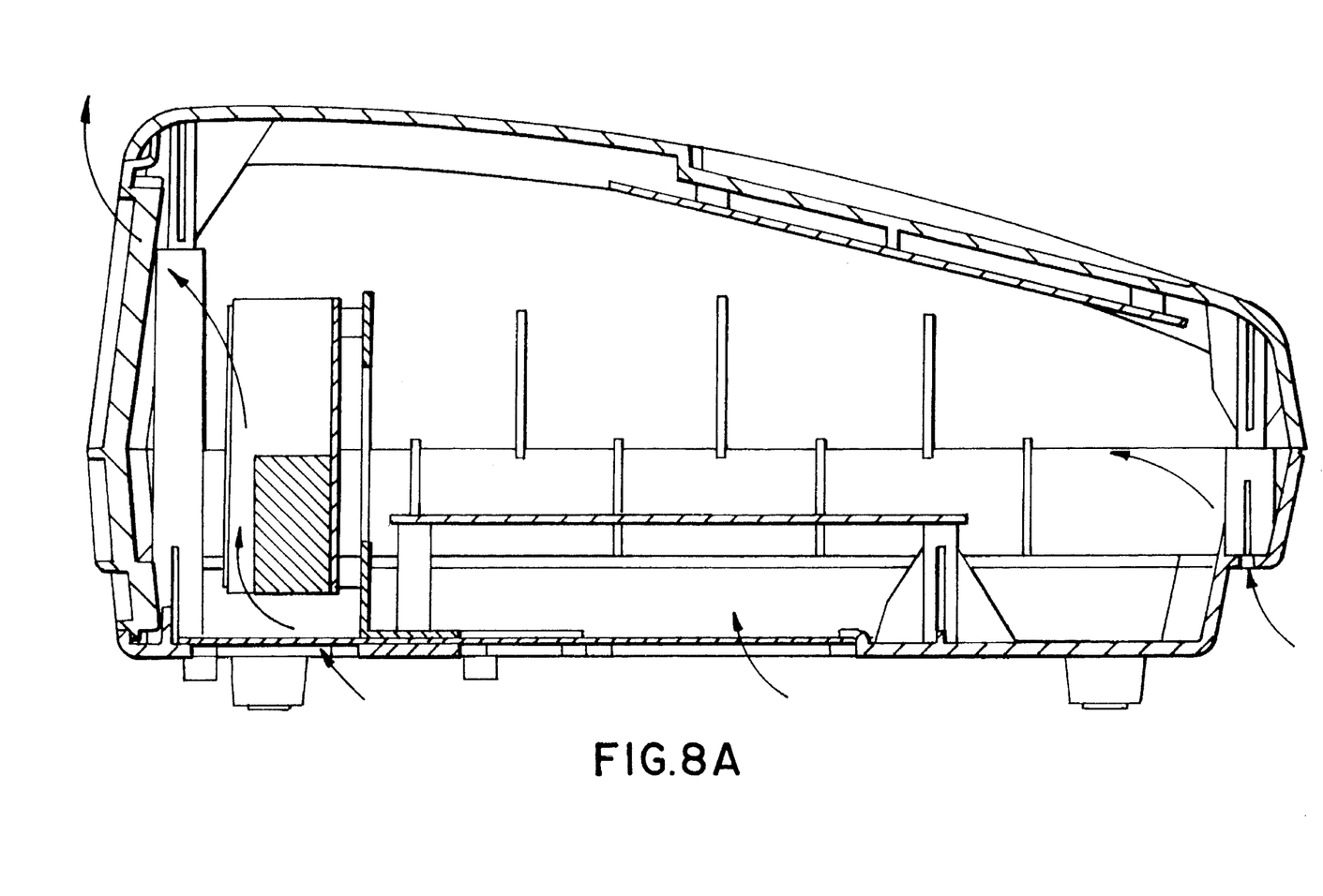
FIG. 8A is a cross-sectional view of the instrument taken along line 8A—8A in FIG. 1A showing the manner in which air can pass through the floor and the front of the housing to dissipate heat.

FIG. 8A is a cut-away view of the instrument showing the manner in which air may enter through the floor and through the forward portion of the instrument and then pass upwardly past the power supply. This natural air convection helps to cool the power supply.

When the instrument is energized the power supply generates heat in the electronic compartment of the instrument. As the heated air rises, cooler outside ambient air is drawn into the electronic compartment through two large openings in the base of the housing. These openings are covered with perforated metal plates which prevent any large hazardous particles from falling outside the base of the instrument should a failure occur. Additional cool outside air is drawn into the compartment through a series of holes around the housing base and through the lower portion of the power supply back vent. The power supply is mounted vertically near the power supply vent with the circuit board towards the center of the instrument to direct heated air to the top portion of the power supply vent. Heated air escapes from the instrument through a power supply vent which has stepped, vertical slots to prevent fluid from entering the instrument yet still allows heated air to escape. The housing base has four raised plastic legs into which are inserted rubber-like feet which keep the housing base elevated to allow cool ambient air easy access to rise up through the instrument.

Figure 9:
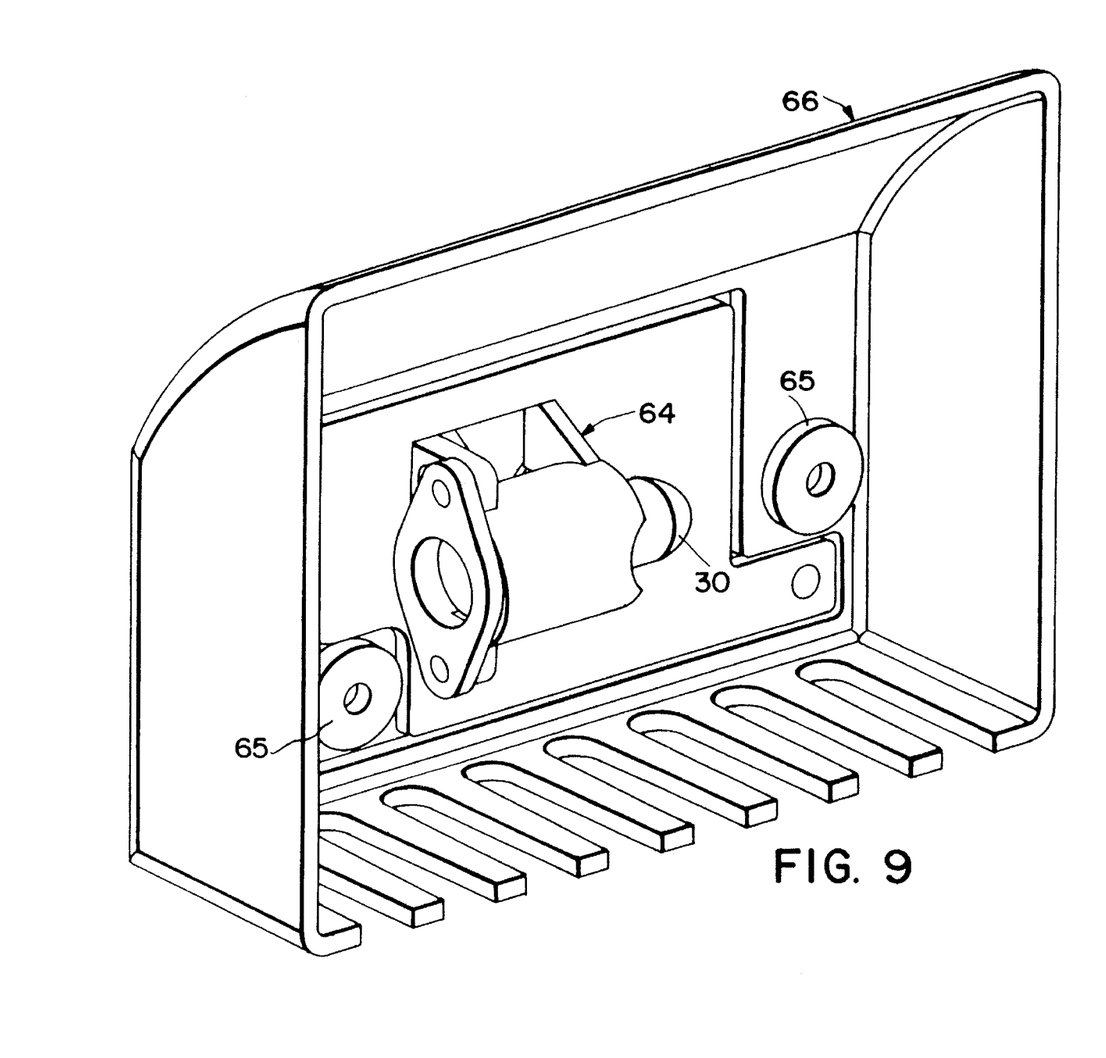
FIG. 9 shows a portion of the housing showing the manner in which the lamp or light source is mounted within the housing.

FIG. 9 shows a holder 64 in which the lamp 30 is detachably mounted. The halogen light source (lamp) 30 is mounted in a high heat-resistance composite material holder 64 which is attached to a high heat-resistance composite material heat shield 66 which is attached to the end of the optics module assembly. The lampholder is further located in the horizontal and vertical direction by two integral tapered locating pins which pass through the heat shield and mate in the tapered holes in the end wall of optics assembly base. The lampholder is located in the light beam axial direction by being attached to a recess area in the heat shield by two miniature screws. The heat shield is located in the light axial direction by two circular recessions 65 on the backside of the shield mating against two circular protrusions on the end wall of the optics assembly base. These location pads also act as attachment points of the heat shield to the optics base by utilizing two miniature screws.

The light source (lamp) is located in the lampholder by four small ribs inside the cylindrical area which rests upon the base of the lamp. These four ribs locate the lamp in the vertical and axial direction. The lamp filament is located in the radial direction in the lampholder by a larger rib inside the cylindrical portion which mates with a groove in the lamp base. The lamp is located in the horizontal direction by a lip inside the cylindrical portion upon which the lamp base near the glass envelope rests and is held tightly against this lip by a retainer which contacts the wire lead end of the lamp base and is attached to the cylindrical portion of the lamp holder by two miniature screws. The entire lamp holder assembly is easily removed and replaced by removing two small screws attaching the assembly to the heat shield.

Figure 10:
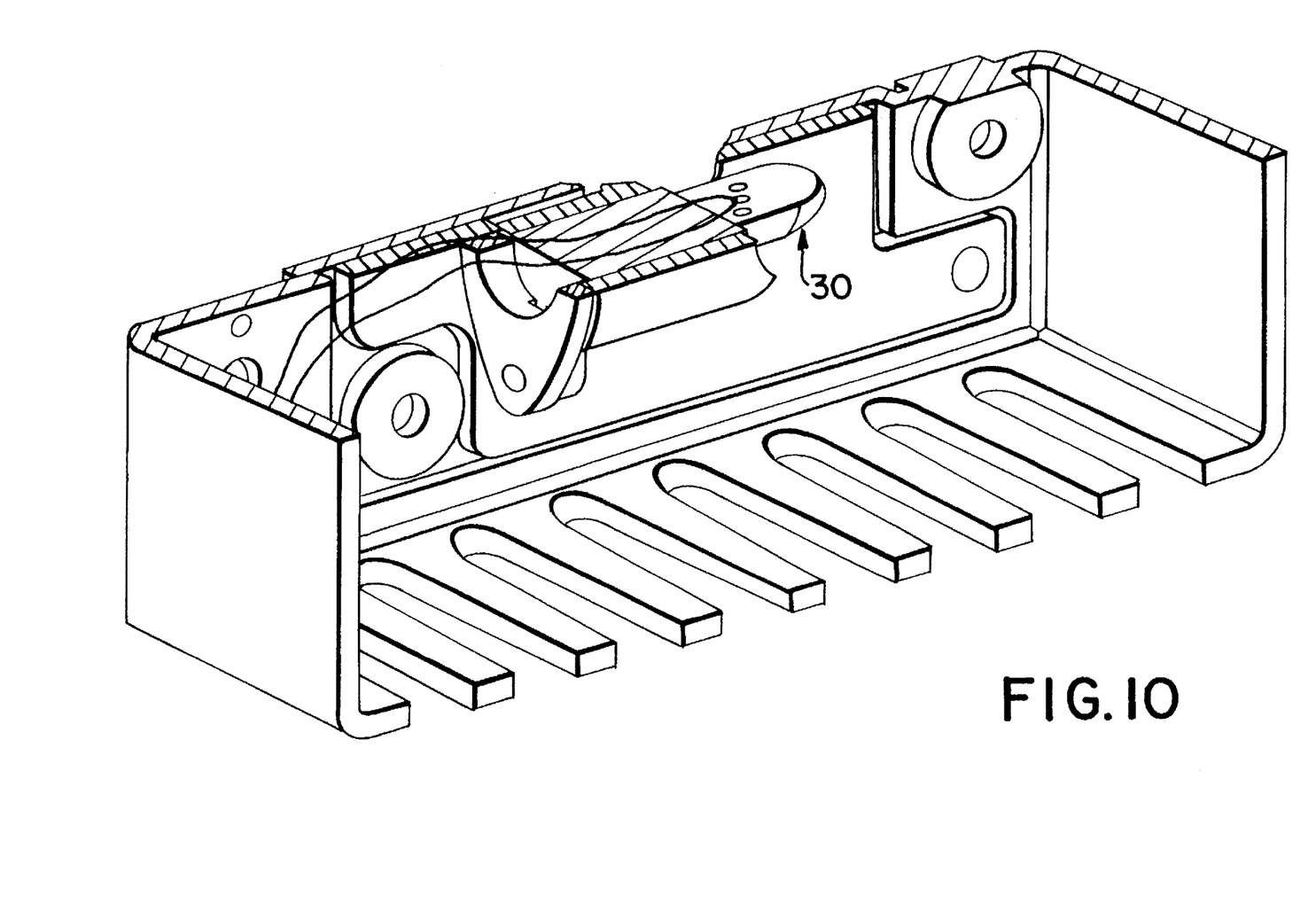
FIG. 10 is a cross-sectional view of a portion of the housing showing the manner in which the lamp or light source is mounted.

FIG. 10 is a cross-sectional view of the lamp holder and lamp.

Figure 10A:
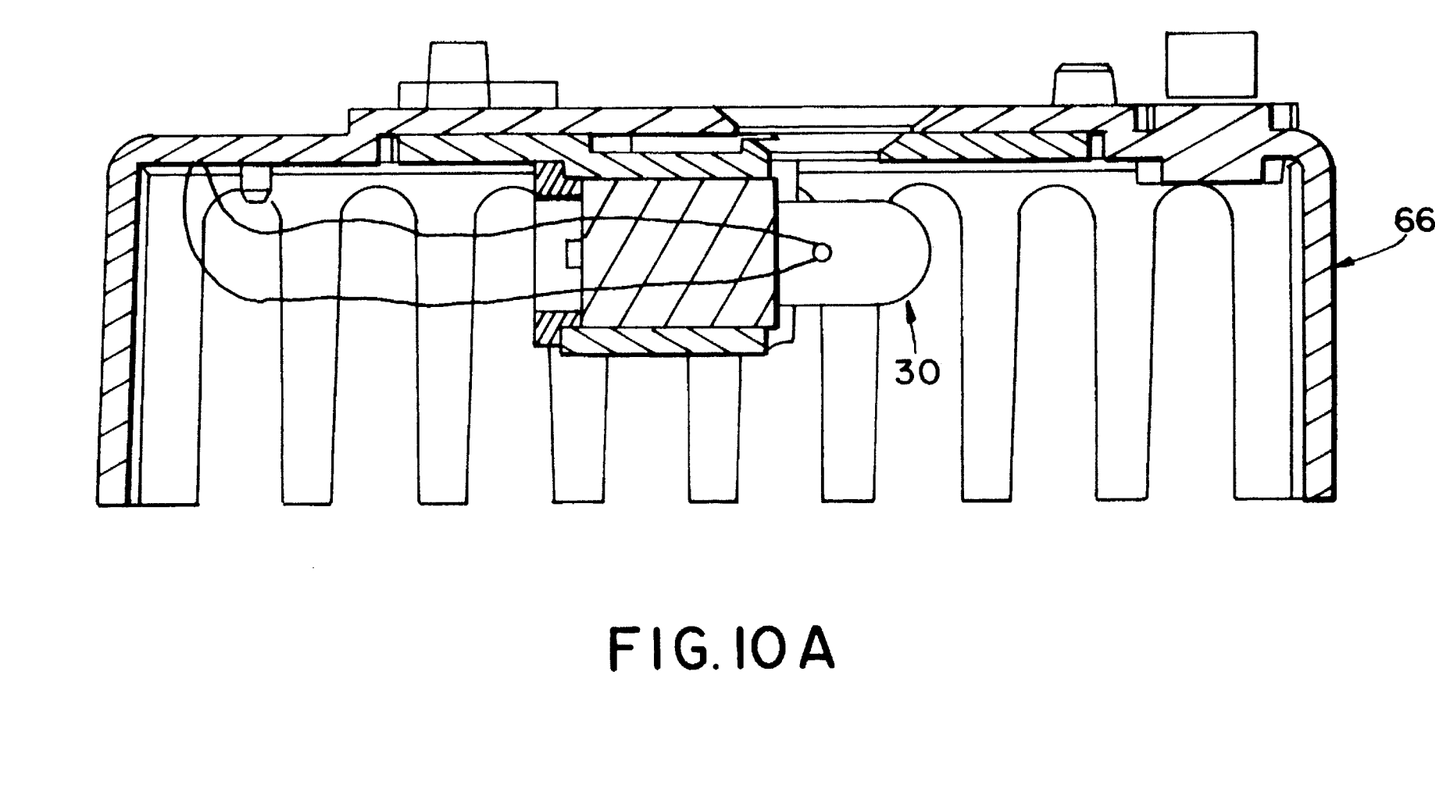
FIG. 10A is another cross-sectional view showing the lamp in the holder.

FIG. 10A is another cross-sectional view of the lamp holder and lamp.

Figure 11:
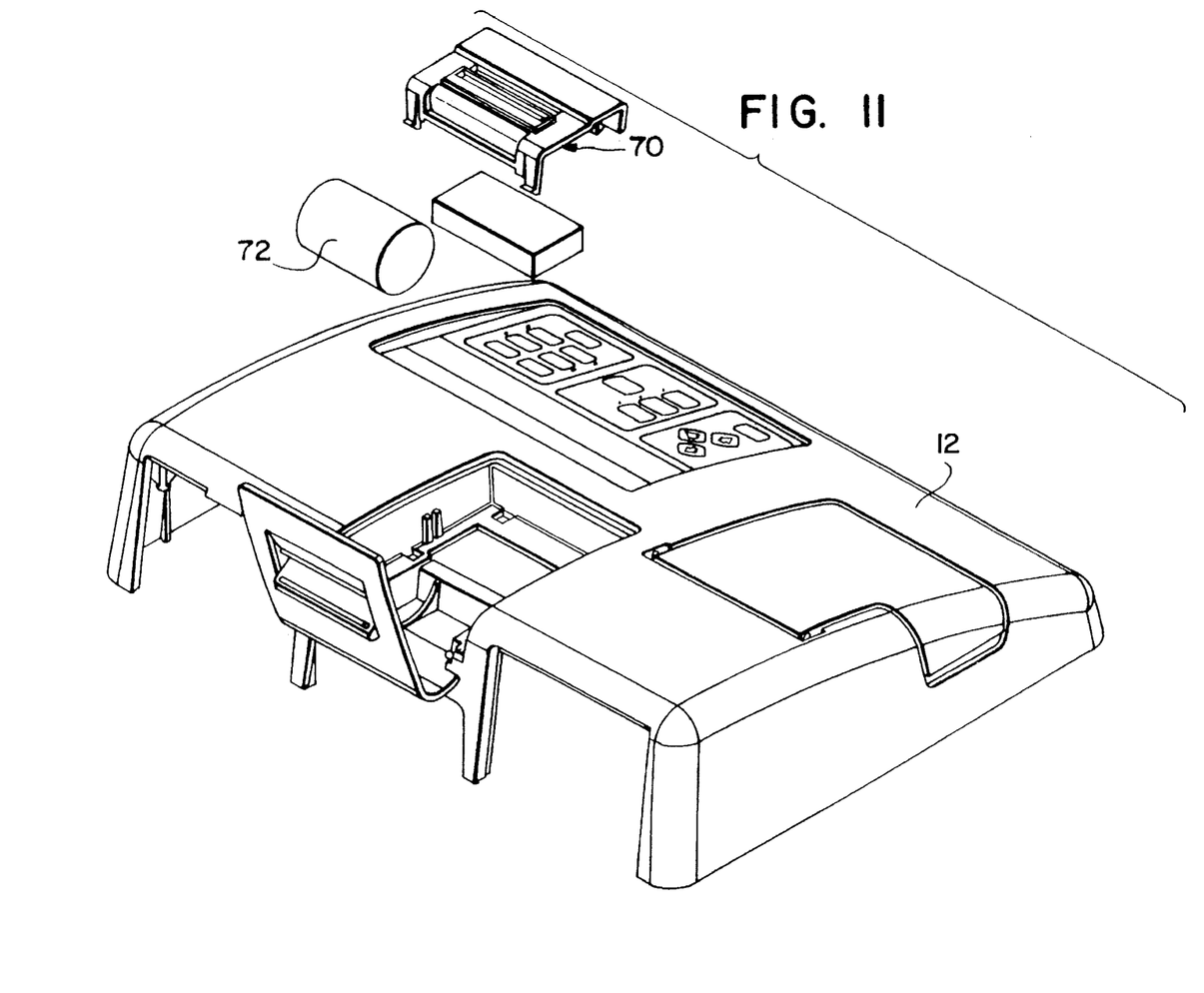
FIG. 11 is an explosion view of the upper portion of the housing showing the manner in which the printer is mounted.

FIG. 11 is an explosion view showing the upper housing member 12, integral printer 70, and paper roll 72.

The nephelometer is provided with an integral paper printer. The printer is nested in the center section of the upper enclosure and retained in the vertical direction by a separate piece. The paper roll is also rested in the center section of the upper enclosure and is fed through the printer, through the printer retainer and through a detachable, pivoted door to exit, the instrument on the top near the back. The exit slot in the door is shaped to guide the used paper to the back of the enclosure away from the key pad and the same exit slot contains an integral saw-toothed edge which acts as a paper cutter. In addition, the exit slot has a raised area to grasp for opening the door to replace paper or service the printer and to assist in guiding the paper up and away from the instrument.

The door pivots on two circular pins which fit into mating holes in the upper enclosure. One pin on the door has two flats near the end which mate into a corresponding slot into the upper enclosure to provide easy assembly and also if the door receives excessive load or force on it during use, the flats act as a failure point instead of deforming or breaking the upper enclosure.

The separate piece used to retain the printer includes four flexible arms with a hook on the end of each arm which mate into four cutouts in the upper enclosure. These hooks along with a rib on the underside of the separate piece hold the printer in the vertical direction. This same rib mates into a slot in the upper enclosure to hold the retainer in the light beam axial direction.

Figure 12:
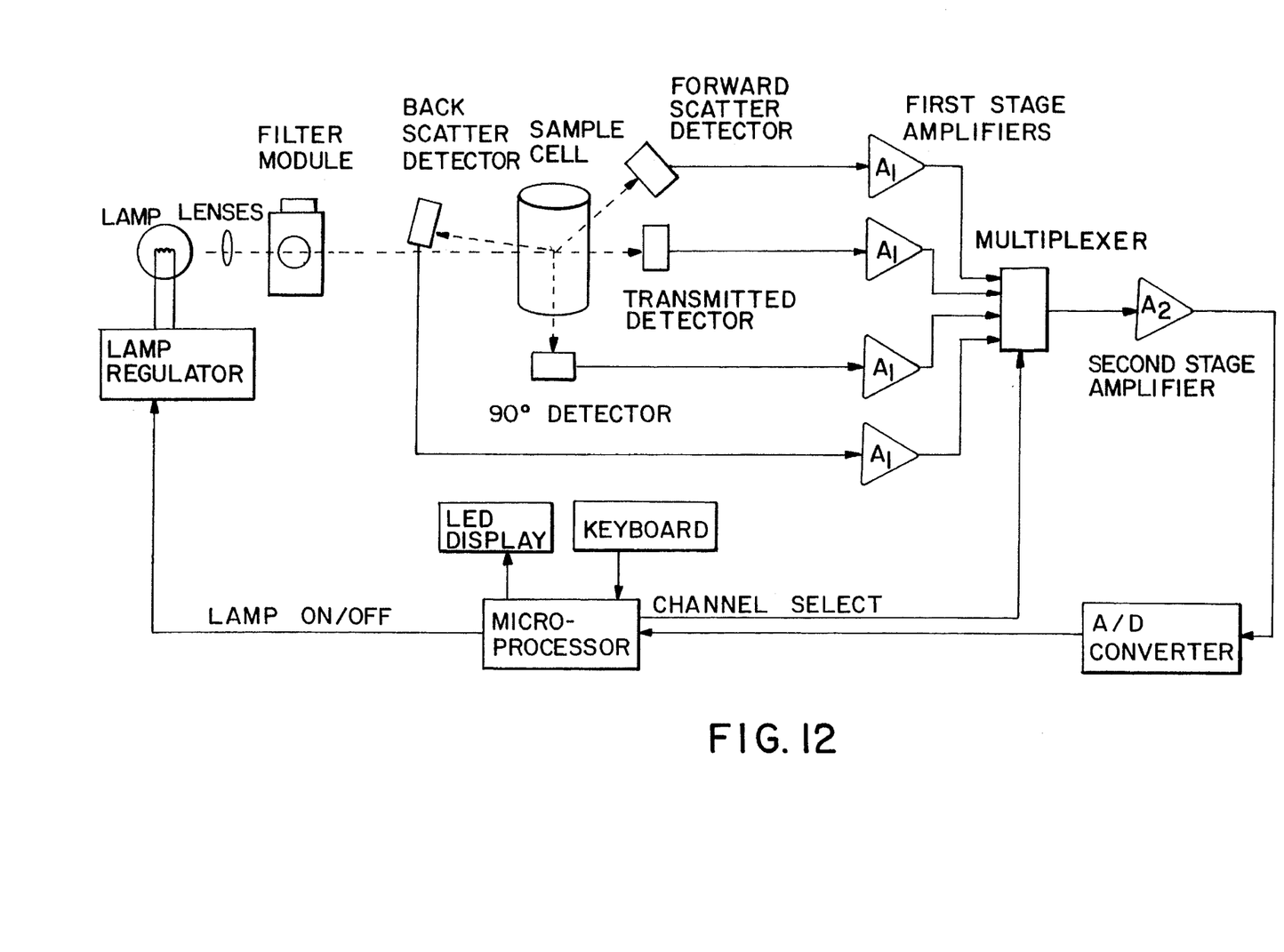
FIG. 12 is a schematic diagram showing the operation and components of the instrument of FIG. 1.

FIG. 12 is a block diagram showing the components included in the instrument 10 and the manner in which they are connected for operation.

To obtain a reading, the microprocessor first ensures that the lamp is on, then the microprocessor sets the multiplexer to the first detector channel so that the analog equivalent voltage of the detector is amplified by operational amplifiers A1 and A2 and is present at the A/D converter. The microprocessor then instructs the A/D converter to convert the analog detector current to its digital equivalent which is stored in the microprocessor's RAM memory. This detector read/store sequence is repeated for each of the four detectors. Finally, the microprocessor computes a reading based on the current reading units and the stored detector values and sends this reading to the LED display.

In the ratio turbidity mode of operation, the displayed value is derived from the four detectors by processing them as a ratio of the 90 degree detector signal to a weighted sum of the transmitted, forward-scatter, and back-scatter detector in this ratio that makes possible the direct measurement of fluids up to 10,000 NTU.

One suitable four-point ratio calibration algorithm is defined as:

$$T = \frac{I_{90}}{d_0 \cdot I_t + d_1 \cdot I_{fs} + d_2 \cdot I_{bs} + d_3 \cdot I_{90}}$$

where

T=Turbidity in NTU Units (0–10,000)

$d_0$, $d_1$, $d_2$, $d_3$=Calibration Coefficients $I_{90}$=Ninety Degree Detector Current $I_t$=Transmitted Detector Current $I_{fs}$=Forward Scatter Detector Current $I_{bs}$=Back Scatter Detector Current Solving for the 4 calibration coefficients is achieved using a system of 4 equations and 4 unknowns, with the following turbidity value substituted into each of the 4 equations:

$T_0$=200 NTU (nominally)

$T_1$=1000 NTU (nominally)

$T_2$=4000 NTU (nominally)

$T_3$=7500 NTU (nominally)

The coefficients are computed automatically after an NTU calibration sequence.

Other variants are possible without departing from the scope of this invention.

What is claimed is:

1. A method for determining the turbidity of a liquid in a sample cell, wherein a light beam is directed into said cell, the method comprising the steps of:

(a) providing a first light detector for receiving light scattered at right angles from a region in said cell illuminated by the light beam and producing a first signal;

(b) providing a second light detector for receiving forward-scattered light through said cell and producing a second signal;

(c) providing a third light detector for receiving light transmitted through said cell and producing a third signal;

(d) providing a fourth light detector for receiving back-scattered light from said cell and producing a fourth signal;

(e) calculating turbidity with an algorithm wherein said first signal is in the numerator and said second, third and fourth signals are in the denominator.

* * * * *